(12) United States Patent
Navarro-Quirante et al.

(10) Patent No.: US 11,406,847 B2
(45) Date of Patent: Aug. 9, 2022

(54) PROTON LINEAR ACCELERATOR SYSTEM FOR IRRADIATING TISSUE WITH TWO OR MORE RF SOURCES

(71) Applicant: ADAM S.A., Meyrin (CH)

(72) Inventors: Jose Luis Navarro-Quirante, Eindhoven (NL); Yevgeniy Ivanisenko, Eindhoven (NL)

(73) Assignee: ADAM S.A., Meyrin (CH)

( * ) Notice: Subject to any disclaimer, the term of this patent is extended or adjusted under 35 U.S.C. 154(b) by 103 days.

(21) Appl. No.: 17/049,807

(22) PCT Filed: Apr. 24, 2019

(86) PCT No.: PCT/EP2019/060471
§ 371 (c)(1),
(2) Date: Oct. 22, 2020

(87) PCT Pub. No.: WO2019/206969
PCT Pub. Date: Oct. 31, 2019

(65) Prior Publication Data
US 2021/0236853 A1    Aug. 5, 2021

(30) Foreign Application Priority Data
Apr. 25, 2018   (EP) ...................................... 18169363

(51) Int. Cl.
*A61N 5/10* (2006.01)
*H05H 7/22* (2006.01)
*H05H 7/02* (2006.01)

(52) U.S. Cl.
CPC ............. *A61N 5/1065* (2013.01); *H05H 7/22* (2013.01); *A61N 2005/1087* (2013.01); *H05H 2007/025* (2013.01); *H05H 2007/227* (2013.01)

(58) Field of Classification Search
CPC .......... A61N 5/1065; A61N 2005/1087; A61N 5/1077; A61N 2005/1022; H05H 7/22;
(Continued)

(56) References Cited

U.S. PATENT DOCUMENTS 5,382,914 A    1/1995 Hamm et al.
9,750,123 B1 *  8/2017 Heath ...................... H05H 7/22
(Continued)

FOREIGN PATENT DOCUMENTS

WO        2015/175751 A1    11/2015
WO        2018/043709 A1     3/2018
WO    WO-2019206967 A1 *  10/2019   ........... A61N 5/1065

OTHER PUBLICATIONS

International Search Report issued in PCT/EP2019/060471; dated Jun. 28, 2019.
(Continued)

*Primary Examiner* — Marcus H Taningco
(74) *Attorney, Agent, or Firm* — Studebaker & Brackett PC

(57) ABSTRACT

Proton beams are a promising alternative to X-rays for therapeutic purposes because they may also destroy cancer cells, but with a greatly reduced damage to healthy tissue. The energy dose in tissue may be concentrated at the tumor site by configuring the beam to position the Bragg Peak proximate the tumor. The longitudinal range of a proton beam in tissue is generally dependent upon the energy of the beam. However, after switching energies, the proton-beam system requires some time for the beam energy to stabilize before it may be used for therapy. A proton linear accelerator system is provided for irradiating tissue with an improved beam energy control, configured to provide RF energy from a first RF energy source during the on-time of the proton beam operating cycle for changing the energy of the proton beam, and to provide RF energy from a second distinct RF energy source during the off-time of the proton beam operating cycle for increasing or maintaining the temperature of the cavity. Each RF source is operated independently, allowing higher RF pulse rates to reach the cavity, supporting a smaller time between proton beam energy pulses. In addi-
(Continued)

tion, the peak power requirements for the second RF energy source may, in general, be less than for the second RF energy source, allowing a less costly type to be used for the second source. The use of a first and second RF source may reduce the cavity settling time from minutes to less than 10 seconds.

15 Claims, 8 Drawing Sheets

(58) Field of Classification Search
CPC ....... H05H 2007/025; H05H 2007/227; H05H 7/02; H05H 9/041
See application file for complete search history.

(56) References Cited

U.S. PATENT DOCUMENTS

| | | | |
|---|---|---|---|
| 10,420,201 B2* | 9/2019 | Nighan, Jr. | H05H 9/048 |
| 2006/0170381 A1* | 8/2006 | Amaldi | H05H 13/00 |
| | | | 315/502 |
| 2007/0108922 A1* | 5/2007 | Amaldi | H05H 6/00 |
| | | | 315/502 |
| 2011/0176648 A1* | 7/2011 | Rowland | H05H 3/06 |
| | | | 376/114 |
| 2011/0286564 A1* | 11/2011 | Johnson | G21G 1/08 |
| | | | 376/156 |
| 2015/0245462 A1* | 8/2015 | Nighan, Jr. | H05H 9/048 |
| | | | 378/138 |
| 2021/0243878 A1* | 8/2021 | De Michele | H05H 9/047 |

OTHER PUBLICATIONS

IPRP and Written Opinion issued in PCT/EP2019/060471; dated Oct. 27, 2020.

* cited by examiner

PROTON LINEAR ACCELERATOR SYSTEM FOR IRRADIATING TISSUE WITH TWO OR MORE RF SOURCES

CROSS-REFERENCE TO RELATED APPLICATIONS

This application is the U.S. National Stage of International Application No. PCT/EP2019/060471 filed Apr. 24, 2019, which claims benefit of priority to European Patent Application No. 18169363.1 filed Apr. 25, 2018, the entire contents of which are incorporated herein by reference.

FIELD OF THE INVENTION

The invention relates to a proton linear accelerator system for irradiating tissue comprising a proton source for providing a proton beam during operation.

BACKGROUND OF THE INVENTION

Energetic beams, such as X-rays, have been used therapeutically for many years to damage the DNA of cancer cells and to kill them in humans and animals. However, during the treatment of tumors, the X-rays expose surrounding healthy tissues, particularly along the path of the X-rays through the body, both before (entrance dose) and after (exit dose) the tumor site. The X-ray dose is frequently sufficiently high to result in short-term side effects and may result in late carcinogenesis, growth dysfunction in the healthy tissue and growth retardation in the case of children.

Proton beams are a promising alternative because they may also destroy cancer cells, but with a greatly reduced damage to healthy tissue. The energy dose in tissue may be concentrated at the tumor site by configuring the beam to position the Bragg Peak proximate the tumor, greatly reducing the dose on the entrance treatment path, and in many cases almost completely eliminating the exit dose on the treatment path. The longitudinal range of a proton beam in tissue is generally dependent upon the energy of the beam. Here dose is used to indicate the degree of interaction between the beam and tissue—interaction is minimal until the end portion of the beam range, where the proton energy is deposited in a relatively short distance along the beam path. This reduction in unwanted exposure longitudinally before and after the target site means that improved doses may be delivered without compromising surrounding healthy tissue. This may reduce the length of treatment, by allowing the delivery of a higher differential effective dose to the tumor itself, above and beyond the dose which is absorbed before and after the tumor, and typically reduces side-effects due to the correspondingly lower surrounding dose. It is particularly beneficial when treating tumors located near critical organs or structures such as the brain, the heart, the prostate or the spinal cord, and when treating tumors in children. Its accuracy makes it also particularly effective when treating ocular tumors. In addition, proton beams may be accurately positioned and deflected to provide transverse control of beam paths.

One of the obstacles to the widespread use of proton therapy is the availability of affordable and compact proton sources and accelerators. The energy of the protons used for treatment are usually in the range 50-300 MeV, and more typically in the range 70-250 MeV. Existing sources relying on cyclotrons or synchrotrons are very large, require custom-built facilities, and are expensive to build and maintain. The use of linear accelerators (Linacs) allow the construction of such a compact source which may be installed in existing medical facilities.

The longitudinal position (depth) of the proton energy dose is mainly configured by changing the energies of the protons (usually measured in MeV) in the beam. U.S. Pat. No. 5,382,914 describes a compact proton-beam therapy linac system utilizing three stages to accelerate the protons from the proton source: a radio-frequency quadrupole (RFQ) linac, a drift-tube linac (DTL) and a side-coupled linac (SCL). The SCL comprises up to ten accelerator units arranged in a cascade, each unit being provided with an RF energy source. The treatment beam energy is controlled by a coarse/fine selection system—in the coarse adjustment, turning one or more of the accelerator units off provides eleven controlled steps from 70 MeV to 250 MeV, with each step being approximately 18 MeV. Fine adjustment of the beam energy between these steps is performed by inserting degrading absorbers, such as foils, into the beam.

The disadvantage of such a system is that after each switching step, the proton-beam system requires some time for the beam energy to stabilize before it may be used for therapy. In addition, the actuation systems for the degrading foils are often unreliable, and the foils must be regularly replaced.

OBJECT OF THE INVENTION

It is an object of the invention to provide a proton linear accelerator system for irradiating tissue with an improved beam energy control.

SUMMARY OF THE INVENTION

A first aspect of the invention provides a proton linear accelerator system for irradiating tissue, the accelerator system comprising: a proton source for providing a pulsed proton beam during operation; a beam output controller for adjusting the beam current of the proton beam exiting the source; an accelerator unit having: a proton beam input for receiving the proton beam; a proton beam output for exiting the proton beam; a first RF energy source for providing RF energy during operation; and second RF energy source, distinct from the first source, for providing RF energy during operation; at least one cavity extending from the proton beam input to the proton beam output, for receiving RF energy from the first and/or second energy source, and for coupling the RF energy to the proton beam as it passes from the beam input to the beam output; the system further comprising: an RF energy controller connected to the first and second RF energy source for adjusting the RF energy provided to the at least one cavity and further connected to the beam output controller; the beam output controller being configured to provide proton beam pulses with a predetermined and/or controlled beam operating cycle; the RF energy controller being configured to provide RF energy from the first RF energy source during the on-time of the proton beam operating cycle for changing the energy of the proton beam, and to provide RF energy from the second RF energy source during the off-time of the proton beam operating cycle for increasing or maintaining the temperature of the cavity.

During operation of the system for proton therapy, the damage to surrounding tissue may be reduced by changing the beam energy, and therefore both the range of the beam and the corresponding Bragg peak. By adjusting the depth of the Bragg peak many separate Bragg peaks may be overlapped to produce an extended Bragg peak which produces a flat, or approximately flat, dose distribution which covers the tumor region. It is therefore advantageous to have a relatively small time between energy steps as this reduces the total treatment time, thereby reducing the risk of patient movement during treatment. Additionally or alternatively, the number of energy levels available for treatment may be increased, allowing a more accurate control of the spread of energy to surrounding tissues. Additionally or alternatively, movements of the tumor during treatment due to, for example patient breathing, may also be compensated for in real-time to improve the control even further. However, this does require an increase in the rate of RF acceleration pulses that need to be supplied to the cavity during operation.

In addition, providing RF compensation pulses (RF energy during the off-time of the proton beam operating cycle) may increase the RF pulse rate reaching the cavity still further. Applying RF power to the accelerator unit cavities during the proton beam off-time may reduce settling time as these RF compensation pulses may be predetermined and/or controlled to increase or maintain the temperature of the cavity.

The invention is based upon the insight that increasing the pulse rate from a RF source may considerably reduce lifetime and reliability of the RF source. In addition, the higher RF pulse rate means that a more expensive RF source may be required, increasing the cost of the accelerator system. Two distinct RF sources are provided—a first, or primary, RF energy source primarily arranged to provide RF acceleration pulses, and a second, or secondary, RF energy source primarily arranged to provide RF compensation pulses. Each RF source is operated independently, allowing higher RF pulse rates to reach the cavity, supporting a smaller time between proton beam energy pulses. In addition, the peak power requirements for the second RF energy source may, in general, be less than for the second RF energy source, allowing a less costly type to be used for the second source. The use of a first and second RF source may reduce the cavity settling time from minutes to less than 10 seconds.

In a further aspect of the invention, the accelerator system further comprises an RF coupler for transferring RF energy from the first and/or second RF energy source to the at least one cavity, the RF coupler having: a first RF input for receiving RF energy from the first RF source; a second RF input for receiving RF energy from the second RF source; and an RF output for providing RF energy to the at least one cavity.

The use of an RF coupler provides a convenient way to transfer RF energy form either RF source or even both sources at the same time.

In another aspect of the invention, the RF energy controller is further configured to provide RF energy from the first RF energy source as a peak power and further configured to provide RF energy from the second RF energy source as average power.

The first RF source may be further optimized to provide high peak power for the RF acceleration pulses, and the second RF source may be optimized for providing a substantially lower peak power for the RF compensation pulses.

In yet another aspect of the invention, the RF energy controller is further configured to provide substantially the same RF energy for each successive proton beam operating cycle.

The energy reaching the cavity during each successive proton beam operating cycle from the first and second RF sources is kept substantially constant. This may provide a high degree of beam stability with a low settling time, which is particularly advantageous during treatment.

In another aspect of the invention, the RF energy controller is further configured to provide RF energy from the first RF energy source with a first peak power and further configured to provide a successive RF energy from the second RF energy source with a second peak power, the second peak power being substantially less than the first peak power. Additionally or alternatively, the RF energy controller may be configured to provide RF energy from the first RF energy source with a first pulse width and further configured to provide a successive RF energy from the second RF energy source with a second pulse width, the second pulse width being substantially greater than the first pulse width.

In still another aspect of the invention, the accelerator system further comprises: a temperature control system for adapting the temperature of the at least one cavity using a liquid, configured and arranged to increase or maintain the temperature of the at least one cavity during the off-time of the proton beam operating cycle.

Additionally, a liquid-based temperature control system may be used to further improve the temperature compensation and/or stabilization. The combination with RF temperature compensation may allow the use of a simplified temperature control system compared to conventional systems.

These and other aspects of the invention are apparent from and will be elucidated with reference to the embodiments described hereinafter.

DETAILED DESCRIPTION OF THE INVENTION

Figure 1:
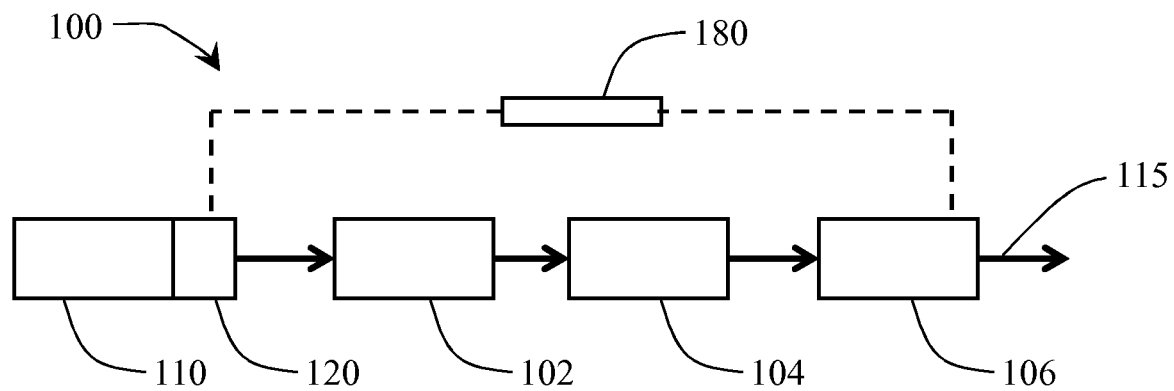
FIG. 1 schematically shows a proton linear accelerator system according to the invention, FIG. 2 schematically depicts an accelerating stage comprising one or more cascaded accelerator units, FIG. 3 schematically depicts an accelerator unit with a cavity to which RF energy may be provided by a first and second RF source.
Figure 5:
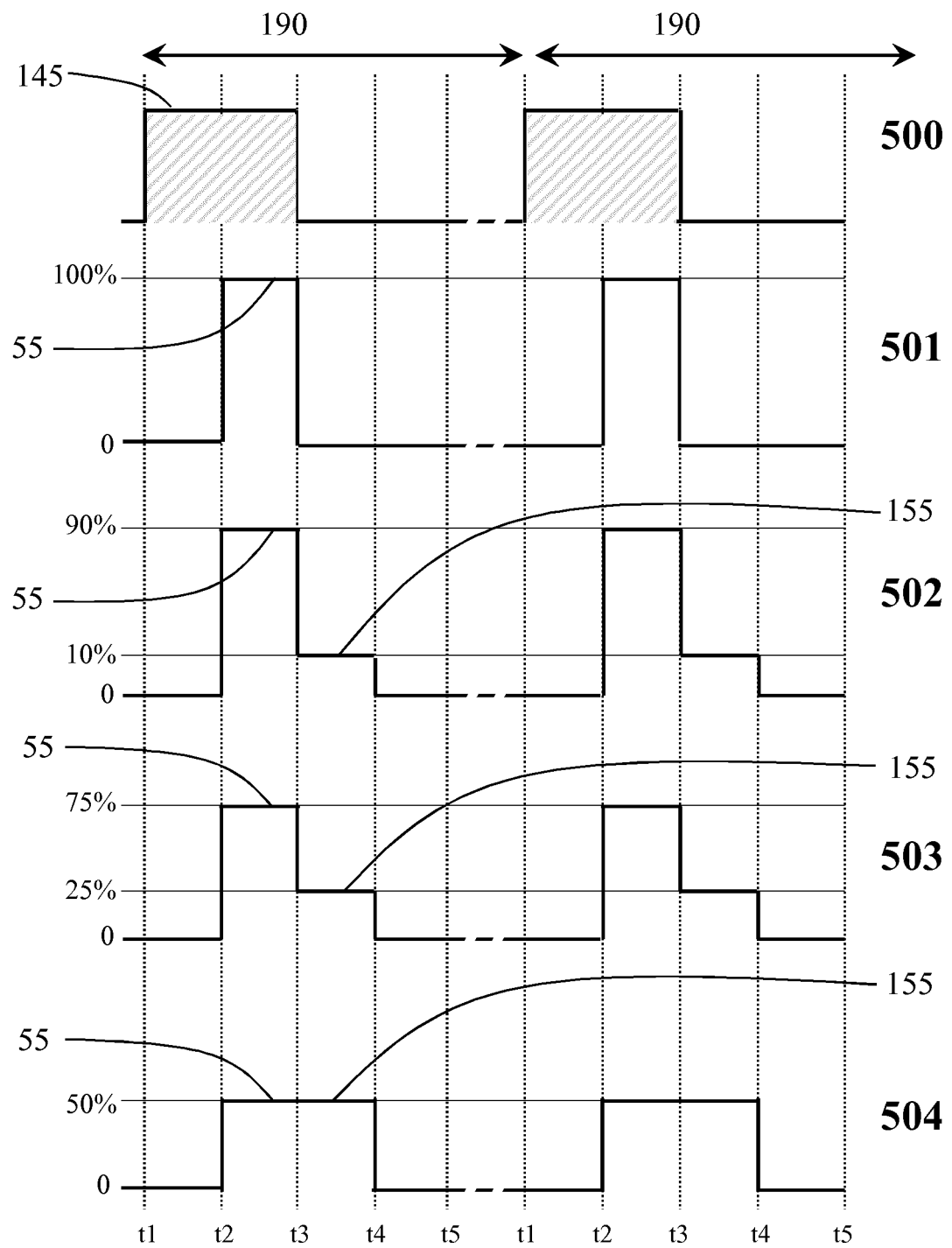
FIG. 5 shows examples of the operation of a first RF source only.
Figure 6:
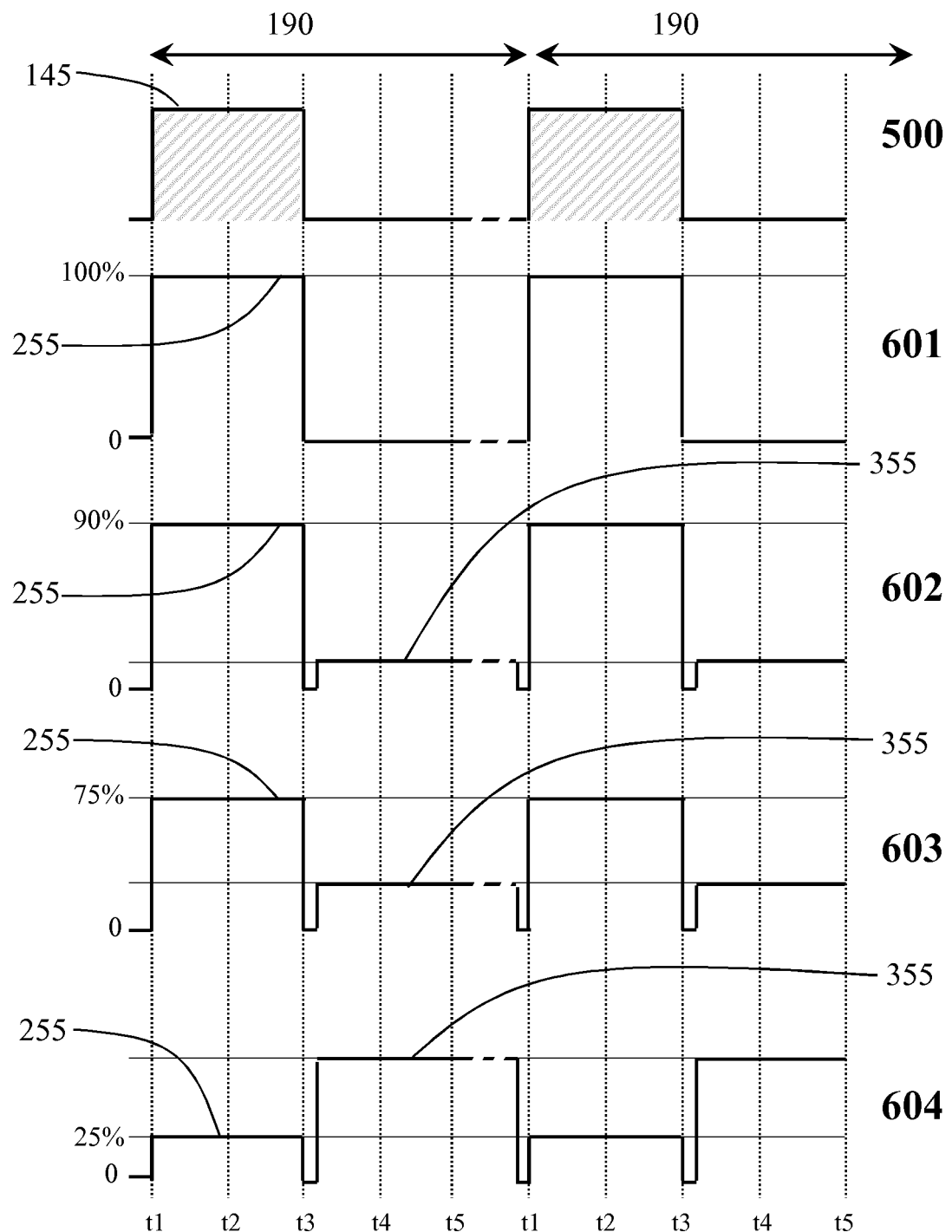
FIG. 6 shows further examples of the operation of a first and second RF source.

FIG. 1 schematically shows a proton linear accelerator (or linac) system 100 according to the invention. The linac system 100 comprises a proton beam source 110 for providing a proton beam 115 during operation. A beam output controller 120 is provided to determine and/or control the beam current of the proton beam exiting the source 110. The proton beam 115 exiting the beam controller 120 is a pulsed beam. It may also be advantageous to configure the beam controller 120 to vary the proton beam duty cycle 145 (depicted in FIGS. 5 and 6). The beam output controller 120 may also be configured to blank the beam for one or more proton beam duty cycles 145, 245 As depicted in FIGS. 5 and 6, the operating cycle 190 of the proton beam 115 usually comprises an on-time and an off-time—the on-time is when the proton beam 115 energy is greater than zero, and the off-time is when the proton beam 115 energy is substantially lower than the on-time energy. The proton beam duty cycle 145 is the on-time expressed as a fraction of the operating cycle 190 period, and often specified as a percentage or ratio. Typically, the energy during the off-time is less than or equal to the minimum energy required for operation of the proton accelerator system 100. The energy during the on-time is usually sufficient for therapeutic purposes and may contribute to the therapeutic dose delivered to the patient.

The proton beam source 110 may comprise other components and sub-components, for example a hydrogen or plasma source, proton accelerating components, intensity modulation components, beam and pulse shaping components etc.

One or more accelerating stages 102, 104, 106 are provided to increase the beam energy to levels typically required for therapy of 50-300 MeV, and more typically in the range 70-250 MeV. Any suitable acceleration techniques may be used that are known to the skilled person.

The proton beam 115 exiting the beam controller 120 enters the first accelerating stage 102. In this particular embodiment, the first stage 102 may be provided by an RFQ (Radio-Frequency Quadrupole) which accelerates the beam up to approximately 3 to 10 MeV, preferably 5 MeV. The main purpose of the RFQ is to keep the beam focused during the first stage of acceleration, and to convert a continuous beam into a bunched one.

In a first example, a suitable RFQ 102 may operate at a frequency of 750 MHz, with a vane-to-vane voltage of 68 kV, a beam transmission of 30% and a required RF peak power of 0.4 MW. In a second example, a suitable RFQ 102 may operate at a frequency of 499.5 MHz, with a vane-to-vane voltage of 50 kV, a beam transmission of 96% and a required RF peak power of 0.2 MW.

The RFQ 102 may also be configured to operate as a beam output controller 120—when operated as a "chopper", if there is no beam controller associated with the source, in which case a pulsed proton beam 115 may still be provided using a continuous proton source 110. The beam output controller function described above may then be partially or fully integrated into the RFQ 102, or control may be distributed between the RFQ 102 and the proton source 110.

The proton beam 115 exiting the first accelerating stage 102 enters the second accelerating stage 104. In this particular embodiment, the second stage 104 may be provided by one or more SCDTLs (Side Coupled Drift-Tube Linac) which accelerate the beam up to approximately 25 to 50 MeV, preferably 37.5 MeV. As an example, a suitable SCDTL 104 may operate at 3 GHz and four of these SCTDLs may be operated in cascade to achieve the 37.5 MeV acceleration.

The proton beam 115 exiting the second accelerating stage 104 enters the third accelerating stage 106, which comprises one or more cascaded accelerator units 130

Figure 2:
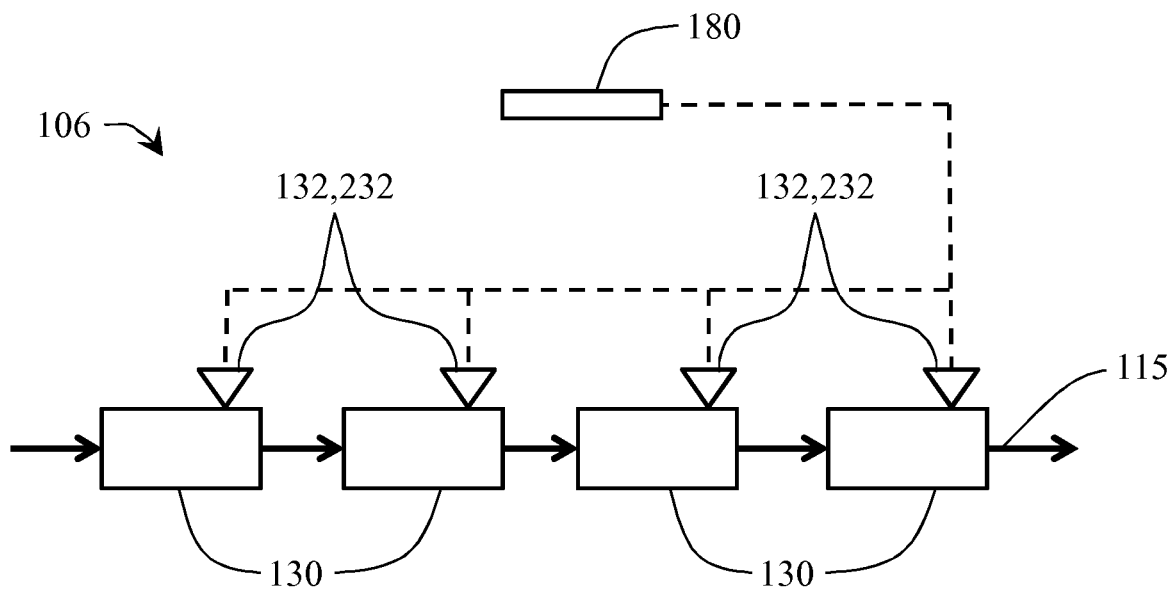
Figure 3:
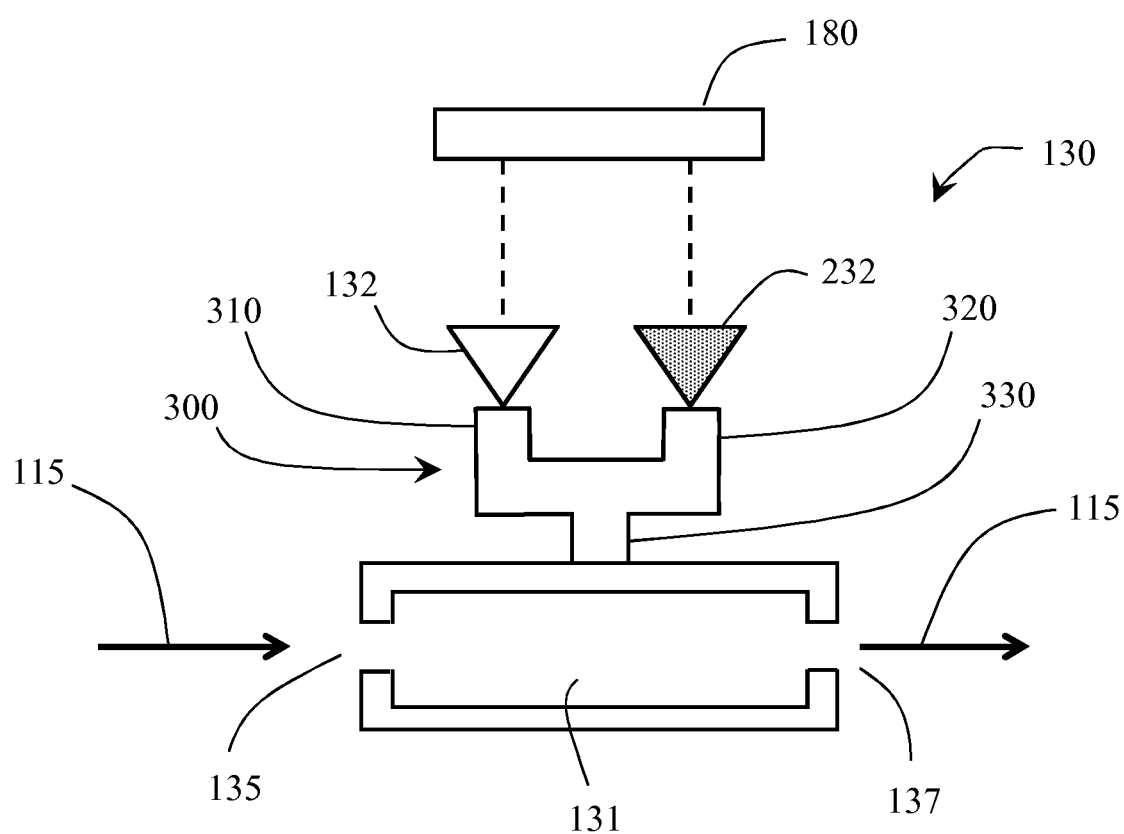

FIG. 2 depicts more details of the third accelerating stage 106 of FIG. 1 and FIG. 3 depicts cascaded accelerating units 130 in the third accelerating stage 106.

In this particular embodiment, the third stage 106 may be provided by one or more CCLs (Coupled Cavity Linac) 130 which accelerate the beam up to the maximum energy of the system 100. This is approximately 50-300 MeV, and more typically in the range 70-250 MeV. As an example, a suitable CCL 130 may operate at approximately 3 GHz, and ten of these CCLs units may be operated in cascade to achieve the 230 MeV acceleration, each CCL providing 20 MeV acceleration.

The accelerator system 100 further comprises an RF energy controller 180 connected to one or more of the RF energy sources 132, 232. The controller is configured and arranged to adjust the RF energy provided one or more cavities of one or more accelerating units 130. The controller 180 is further connected to the beam output controller 120, and configured and arranged to provide RF energy from RF energy sources 132, 232 during the on-time and off-time of the proton beam operating cycle 190.

The proton beam 115 which emerges from the third accelerating stage 106 is typically guided into a high energy beam transfer line, comprising bending magnets, to steer the beam into a nozzle for application to the patient during treatment.

The proton beam 115 is usually delivered to the patient in therapeutic on-time pulses of a predetermined and/or controlled duration (typically between a few microseconds and a few milliseconds) at a predetermined and/or controlled repetition frequency (typically between 100 and 400 Hz). In cases where the therapeutic on-time is greater than the repetition period of the proton source 110, the proton beam duty cycle 145, 245 is the product of the therapeutic pulse on-time duration 145 and the repetition frequency of the proton source 110. In cases where the therapeutic on-time is less than or equal to the repetition period of the proton source 110, the proton beam duty cycle 145, 245 is determined by the therapeutic pulse on-time duration 145, 245.

FIG. 3 schematically depicts an accelerator unit 130, which comprises:
- a proton beam input 135 for receiving the proton beam 115;
- a proton beam output 137 for exiting the proton beam 115;
- a first 132 RF energy source for providing RF energy during operation;
- and second 232 RF energy source, distinct from the first source 132, for providing RF energy during operation;
- at least one cavity 131 extending from the proton beam input 135 to the proton beam output 137 for receiving RF energy from the first 132 and/or second 232 RF energy source, and for coupling the RF energy to the proton beam 115 as it passes from the proton beam input 135 to the proton beam output 137.

The RF energy controller 180 is configured and arranged to control the first 132 and/or second 232 RF energy sources:
- to provide RF energy from the first RF energy source 132 primarily during the on-time of the proton beam operating cycle 190 for changing the energy of the proton beam 115, and
- to provide RF energy from the second RF energy source 232 primarily during the off-time of the proton beam operating cycle 190 for increasing or maintaining the temperature of the cavity 131.

During operation, RF energy is provided during the off-time of the proton beam to compensate for the temperature change experienced in the RF cavities 131 between proton beam pulses 145. The instability seen after accelerating units are turned on or off is mainly related to the temperature changes in the cavity 131. Such cavities are typically made of metal, and substantial changes in RF power supplied to the cavity produce temperature changes which cause either contraction or expansion of the cavity. As the cavity supports tuned electromagnetic waves, any thermal expansion or contraction will tune the cavity off-resonance and disrupt the proton beam 115.

Providing RF energy for compensation may be advantageous when successive RF energy acceleration pulses, provided during the on-time of the proton beam, provide similar or identical power levels. Following off-time, a cavity 131 may need a short period of time to settle once an RF energy acceleration pulse has been applied (on-time). This instability may limit the usable proton beam pulse 145 as an excessive instability in the energy of the proton beam pulses 145 may result in positioning instability of the proton beam during operation. By providing appropriate RF compensation pulses during the proton beam off-time, this settling time may be reduced, or even eliminated.

The RF energy compensation may be particularly advantageous when successive RF energy acceleration pulses, provided during the on-time of the proton beam, provide different power levels to vary the energy of the proton beam pulses. The RF energy for compensation may be predetermined and/or controlled to provide an optimized cavity temperature for a subsequent RF acceleration pulse.

In general, when RF resonant cavities 131 change temperature, the resonant condition changes and the efficiency of the cavity 131 storing RF power may drop. This condition creates undesirable reflections of RF power from the cavity 131.

The efficiency of the cavity 131 may be improved by correcting the temperature of the cavity 131 by providing RF compensation pulses. Alternatively or additionally, the RF frequency of the RF acceleration pulses and/or RF compensation pulses may be modified.

Typically, RF energy sources with a frequency of approximately 3 GHz may be used, for example and RFQ of 2.99792 GHz. The frequency of the RF acceleration pulses is preferably fixed to four times that of the RFQ, as this may provide a high degree of proton beam stability. However, the frequency of the RF compensation pulses has only an indirect effect on the stability of the proton beam, allowing a greater degree of frequency modification.

The use of RF compensation pulses is preferred over liquid-based temperature control systems, which are known in the art to stabilize and adapt the temperature of similar cavities 131—they use heat exchange and are dominated by convection which is a slow process. In a linear accelerator system for therapeutic use, the temperature changes in the cavities 131 may be very fast—the temperature correction system consequently requires a fast response time which is possible using the RF compensation pulses.

Such cavities 131 are typically made of metal, and substantial changes in RF power supplied to the cavity produce temperature changes which cause either contraction or expansion of the cavity. As the cavity supports tuned electromagnetic waves, any thermal expansion or contraction will tune the cavity off-resonance and disrupt the proton beam 115. Off-resonance means the proton beam 115 is not correctly coupled to the RF field in the next and/or subsequent duty cycles 145, 245—the result is a reduction, or even a complete stop, of acceleration. In practice, this may result in the loss of the therapeutic beam during treatment.

For a typical klystron modulator and RF energy source 132, the nominal RF pulse width available for accelerating the beam may be 5 microsecond flattop. For a typical operation of 200 pulses per second, the period of the operating cycle 190 is 5 milliseconds. For example, during operation with a single RF source 132, acceleration pulses of 5 μs (microseconds) and 7.5 MW may be provided by this single RF source 132 during the on-time of the proton beam 115. With an RF pulse rate of 200 Hz, an average power of 7.5 kW may be provided. About 3 kW of average power may reach the cavity 131. Any RF power not absorbed by the proton beam 115 is dissipated on the walls of the cavity 131, producing heat. The conventional water-cooling system absorbs most of the heat excess to reach an equilibrium at the resonant temperature of the cavity. Any change on the RF power will produce too much or too little heat. This heat difference produces dilatation or contraction, and the inner volume of the cavity changes. The resonance condition is then reduced or even lost, and some power is reflected, resulting in a beam having an incorrect energy.

Temperature increase and stabilization using RF energy is dominated by Ohmic losses on the walls of the cavity, which is a faster process. RF energy provided by the second RF energy source 232 increases and/or stabilizes the temperature of the cavity 131, and the degree of increase and/or stabilization may be predetermined and/or controlled by changing the RF power delivered by the second RF energy source 232. Based on measurements on actual cavities where no RF compensation pulses are used, about 1 degrees Centigrade may be lost every 5 to 20 seconds, and approximate 1 minute would be required to recover each lost degree Centigrade.

Preferably, the temperature of the RF cavities 131 is kept substantially constant by providing energy from the second RF energy source 232 to compensate the energy variations of the first RF energy source 132. However, the skilled person will realize that even a partial compensation may also be advantageous as that may reduce the settling time when the proton beam pulse is on. Conventional liquid-based temperature control systems may additionally be used to further improve the temperature compensation and/or stabilization, but the use of RF compensation may simplify any liquid-based temperature control system compared to conventional systems. The use of a first 132 and second 232 RF source as described in this disclosure may reduce the cavity settling time from minutes to less than 10 seconds.

It may be advantageous to use each RF energy source 132, 232 predominantly for its primary purpose, and marginally for its secondary purpose. The primary purpose of the second RF energy source 232 is to be dissipated by Ohmic losses, while the first RF energy source 132 preferably fulfils the operational requirements in terms of amplitude, phase, stability, etc.

The second RF energy source 232 may be less expensive than the first RF energy source 132 as the operational requirements may also be reduced compared to the first RF energy source 132. For example, one or more of the following: a lower peak RF power, a longer pulse width, a lower degree of RF energy stability, a higher RF energy settling time. It may even be a continuous wave (cw) source.

A typical example for medical applications accelerating cavities would be the use of a klystron as a first RF energy source 132, delivering high quality short RF pulses for treatment, and the use of gyrotron or solid-state amplifiers as a second RF energy source 232, for RF energy compensation.

RF energy sources known in the art may limit RF operation to an RF pulse rate of 200 pulses per second, or 200 Hz. For a typical operation of 200 pulses per second, the period of the operating cycle 190 is 5 milliseconds. As each RF source 132, 232 in the invention may be operated independently, a combined higher RF pulse rate may be provided to support a smaller time between proton beam energy pulses.

In addition, the peak power requirements for the second RF energy source may, in general, be less than for the second RF energy source, allowing a less costly type to be used. Typically, pulse rate of the first RF energy source 132 will determine the suitability of a second RF energy source 232 design. The smaller the pulse rate, the bigger the elapsed time between RF acceleration pulses, allowing the choice of a second RF energy source 232 with smaller pulse peak power for the same average power which in general will reduce the price.

The operation of the first 132 and second 232 RF energy sources is synchronized by the RF energy controller 180. Preferably, the second RF energy source 232 is operated in the elapsed time between pulses of the first RF energy source 132 to reduce or even eliminate interference.

For example, the pulse width of the first source 132 when being used to primarily accelerate the beam may be 5 us. The pulse width of the second source 232 when being used to primarily compensate may be 5 ms. In this case, the peak power of the second source 232 may be approximately one thousand times smaller than the peak power of the first one 132 to keep substantially the same average power. So even if the first 132 and second 232 sources operate at the substantially same time (or with a high degree of temporal overlap), the effect of the second source 232 on the proton beam 115 may be substantially insignificant—it may even be negligible. Under such conditions, the second RF source 232 may be a cw (continuous wave) source.

However, the use of more than one distinct RF energy sources 132, 232, means that it may also be advantageous to configure and arrange the RF energy controller 180:
  to provide RF energy from the first RF energy source 132 secondarily during the off-time of the proton beam operating cycle 190 for changing the energy of the proton beam 115, and
  to provide RF energy from the second RF energy source 232 secondarily during the off-time of the proton beam operating cycle 190 for increasing or maintaining the temperature of the cavity 131.

In many cases, the RF energy is configured and arranged for increasing or maintaining the energy of the proton beam 115, for example by using RF amplitude modulation. In some cases, the RF energy may be configured and arranged to reduce the energy of the proton beam 115, for example, by using RF phase modulation.

In this context, distinct means a different device, even if the type of device is the same. They are operated at substantially different times, although in practice due to non-negligible rise and fall times of the pulses, there may be some temporal overlap between the RF pulses from the first 132 and second 232 RF energy sources.

If both RF sources 132, 232 are coupled to the same coupler which allows RF energy to pass from the first 132 and/or second 232 RF energy sources to the same cavity, this is evidence of being distinct. Further, the use of isolators 410, 420 between each RF source and the coupler is further evidence of them being distinct.

If more than one accelerating unit 130 are cascaded, the units are configured and arranged such that proton beam 115 exiting the proton beam output 137 of the upstream accelerating unit 130 may be received by the proton beam input 237 of the downstream accelerating unit 230. Cascaded means that the accelerating units 130 are arranged in sequence, so the proton beam 115 gains a certain amount of energy in each one. This allows a modular approach to choose a suitable number of cavities to define the maximum energy achievable in the system.

The accelerating units 130 may be controlled independently or synchronized as a group.

FIG. 3 further depicts an RF coupler or combiner 300, for transferring RF energy from the first 132 and/or second 232 RF energy source to at least one cavity 131, the RF coupler or combiner 300 having:
  a first RF input 310 for receiving RF energy from the first RF source 132;
  a second RF input 320 for receiving RF energy from the second RF source 232; and
  an RF output 330 for providing RF energy to at least one cavity 131.

The RF coupler or combiner 300 is configured and arranged to allow RF energy transfer from the first RF source 132 and the second RF energy source 232, either alternatively or simultaneously to the cavity 131

The RF energy provided during the proton beam on-time may be varied by modifying one or more of the characteristics of the RF energy emitted by the RF energy source 132, 232 such as RF amplitude, RF phase and/or RF energy pulse shape. Additionally or alternatively, degrading absorbers may also be used, or means to modify the geometry of the cavity and/or the RF coupling. For example, ferrite tuners or mechanical tuners may allow the module to be kept on resonance in spite of the temperature changes.

FIG. 5 depicts the synchronization of four RF energy control configurations 501, 502, 503, 504 using a first RF source 132 only. The proton-beam operating cycle 190 is depicted to illustrate the synchronization of the RF energy control with the proton beam operating cycle 190, and in particular with the proton beam pulses 145.

The RF energy controller 180 is configured and arranged to keep the average power substantially constant by providing separate RF energy pulses during both the proton beam on-time 145 and off-time. This means that the average power supplied to the accelerator cavity 131 is kept substantially constant.

Four waveforms are depicted over two operating cycles 190 of the proton beam pulse 145, including four instants—t1, t2, t3, t4 and t5 for each operating cycle 190. These instants are depicted symmetrically, but in practice the intervals between the instants may vary considerably. The waveforms are depicted as square waves, but in practice the waveforms will have non-negligible rise and fall times which may need to be taken into account.

The top waveform 500 depicts the proton beam pulses 145 during the two operating cycles 190. The beam current rises from zero to its maximum at instant t1 and back to zero at t3 for the on-time of the first beam operating cycle 190, the pulse 145 being of approximately uniform amplitude. Between t3 to the next t1, the beam current (and beam energy) is zero, or approximately zero, for the off-time of this first beam operating cycle 190. The waveform repeats during the second operating cycle 190.

For a typical operation of 100 pulses per second, or 100 Hz, the period of the operating cycle 190 is 10 milliseconds. For a typical operation of 200 pulses per second, or 200 Hz, the period of the operating cycle 190 is 5 milliseconds. The interval t1 to t2 may typically be 2.5 microseconds, and t1 to t3 typically 5 microseconds.

The first RF control configuration graph 501 plots the RF energy provided to the cavity 131 of an acceleration unit 130 over the same period of time. At the start of the first operating cycle 190, the RF energy rises from zero to a reference acceleration peak 55 value at t2 and back to zero at t3, the RF energy pulse 55 being of approximately uniform amplitude. During the rest of this first operating cycle 190, including instants t1 and t4, the RF energy is zero, or approximately zero. The waveform repeats during the second operating cycle 190.

The duration of the RF energy pulse 55 from t2 to t3 and the reference acceleration peak 55 value are predetermined and/or controlled to provide the desired acceleration of the proton beam by the RF energy during the proton beam on-time. Acceleration occurs between t2 & t3. This RF control configuration is the reference for the other three 502, 503, 504 so the reference acceleration peak 55 value is considered here to be nominally 100%. During operation according to 501, the RF energy is provided to the cavity in a single pulse per proton beam operating cycle 190 at substantially the same time as the on-time 145 of the proton beam. No substantial RF energy is provided during the proton beam off-time, so no RF compensation pulses are provided.

The second RF control configuration graph 502 plots the RF energy provided to an acceleration unit 130 over the same period of time. At the start of the first operating cycle 190, the RF energy rises from zero to an acceleration peak 55 value at t2 and back down at t3, the RF energy pulse 55 being of approximately uniform amplitude. This acceleration peak 55 value is approximately 90% of the reference acceleration peak value 501. The RF energy drops to a compensation peak 155 value at t3 and back to zero at t4. This compensation peak 155 value is approximately 10% of the reference acceleration peak value 501. During the rest of this first operating cycle 190, the RF energy is zero, or approximately zero. The waveform repeats during the second operating cycle 190.

The duration of the RF energy pulses 55 from t2 to t3 and the acceleration peak 55 value 90% are predetermined and/or controlled to provide the desired acceleration of the proton beam by the RF energy during the proton beam on-time. Acceleration occurs between t2 and t3.

In general, the duration of the RF energy pulse 155 from t3 to t4, and the compensation peak value 10% are predetermined and/or controlled to compensate for the temperature change which would be expected when the accelerating unit is operated with a lower acceleration peak 55 value compared to previous operating cycles such as in 501. During operation, the RF energy is provided to the cavity in two pulses per proton beam operating cycle 190—the first 55 at substantially the same time as the on-time of the proton beam, and the second 155 at substantially the same time as the off-time of the proton beam.

For the first RF energy source 132, a typical pulse length, such as 5 microseconds, has been divided into two half-pulse, such as 2.5 microseconds. The RF energy controller 180 is configured to provide the first half of this pulse for acceleration, and the second half for compensation.

The third RF control configuration graph 503 plots the RF energy provided to an acceleration unit 130 over the same period of time. At the start of the first operating cycle 190, the RF energy rises from zero to an acceleration peak 55 value at t2 and back down at t3, the RF energy pulse being of approximately uniform amplitude. This first acceleration peak 55 value is approximately 75% of the reference acceleration peak value 501. The RF energy drops to a compensation peak 155 value at t3 and back to zero at t4. This compensation peak 155 value is approximately 25% of the reference acceleration peak value 501. During the rest of this first operating cycle 190, the RF energy is zero, or approximately zero. The waveform repeats during the second operating cycle 190.

The duration of the RF energy pulses 55 from t2 to t3 and the acceleration peak 55 value 75% are predetermined and/or controlled to provide the desired acceleration of the proton beam by the RF energy during the proton beam on-time. Acceleration occurs between t2 & t3.

In general, the duration of the RF energy pulse 155 from t3 to t4, and the compensation peak value 25% are predetermined and/or controlled to compensate for the temperature change which would be expected when the accelerating unit is operated with a lower acceleration peak 55 value compared to previous operating cycles such as 501 or 502. During operation, the RF energy is provided to the cavity in two pulses per proton beam operating cycle 190—the first 55 at substantially the same time as the on-time of the proton beam, and the second 155 at substantially the same time as the off-time of the proton beam.

Note that the same power would be provided to the cavity if the levels were reversed—if the acceleration peak 55 value is 25% and the compensation peak 155 value is 75%, although a significantly lower degree of proton beam 115 acceleration would be provided.

The fourth RF control configuration graph 504 plots the RF energy provided to an acceleration unit 130 over the same period of time. At the start of the first operating cycle 190, the RF energy rises from zero to an acceleration peak 55 value at t2 and remains at the compensation peak 155 value at t3, the RF energy pulse being of approximately uniform amplitude. This first acceleration peak 55 value is approximately 50% of the reference acceleration peak value 501. The compensation peak 155 value is also approximately 50% of the reference acceleration peak value 501, so it stays at this value at t3, and drops to zero at t4. During the rest of this first operating cycle 190, the RF energy is zero, or approximately zero. The waveform repeats during the second operating cycle 190.

The duration of the RF energy pulses 55 from t2 to t3 and the acceleration peak 55 value 50% are predetermined and/or controlled to provide the desired acceleration of the proton beam by the RF energy during the proton beam on-time. Acceleration occurs between t2 & t3.

In general, the duration of the RF energy pulse 155 from t3 to t4, and the compensation peak value 50% are predetermined and/or controlled to compensate for the temperature change which would be expected when the accelerating unit is operated with a lower acceleration peak 55 value compared to previous operating cycles such as 501, 502 and 503. During operation, the RF energy is provided to the cavity in two pulses per proton beam operating cycle 190—the first 55 at substantially the same time as the on-time of the proton beam, and the second 155 at substantially the same time as the off-time of the proton beam.

In these example, the pulse durations of the compensation 155 and acceleration pulses 55 are the same, so by ensuring that the peak values of the uniform amplitude compensation 155 and acceleration 55 pulses add up to 100% of the reference peak value 501, the RF energy provided to the cavity for each successive operating cycle 190 is substantially the same in 501, 502, 503 and 504. These stepped pulses are predetermined and/or controlled to have the same area under the power curve as the single flattop depicted in 501.

Although the acceleration peaks 55 and compensation peaks 155 are drawn and described as contiguous, the RF controller 180 may also be arranged and configured to provide compensation peaks 155 separate from the acceleration peaks 55—in other words, there may be a delay between them when the RF energy is zero, or approximately zero. The acceleration peaks 55 would then return to zero at t3, and the compensation peaks 155 may, for example, rise from zero at t4 and return to zero at t5. The compensation peaks 155 are preferably arrange midway between the acceleration peaks 55—this may provide a high degree of efficiency.

So substantially constant average power may be achieved by interspersing the compensating pulses, during the proton beam off-time, between the accelerating pulses, during the proton beam on-time 145. The time between RF energy pulses are preferably short compared to the thermal time response of the cavity. The amplitude of the accelerating pulse 55 may be varied over the full range from maximum power to nearly zero power. Likewise, the power in the compensation pulse 155 may be varied from maximum power to nearly zero power to keep the average power substantially constant.

FIG. 6 depicts the synchronization of four RF energy control configurations 601, 602, 603, 604 using a first RF source 132 for the acceleration peaks 55, and a second RF source 232 for the compensation peaks 155. The proton-beam operating cycle 190 is depicted to illustrate the synchronization of the RF energy control with the proton beam operating cycle 190, and in particular with the proton beam pulses 145.

The RF energy controller 180 is configured and arranged to keep the average power substantially constant by providing separate RF energy pulses during both the proton beam on-time 145 and off-time.

Four waveforms are depicted over two operating cycles 190 of the proton beam pulse 145, including four instants—t1, t2, t3, t4 and t5 for each operating cycle 190. These instants are depicted symmetrically, but in practice the intervals between the instants may vary considerably. The waveforms are depicted as square waves, but in practice the waveforms will have non-negligible rise and fall times which may need to be taken into account.

The top waveform 500 depicts the proton beam pulses 145 in the same way as depicted in FIG. 5.

The first combined RF control configuration graph 601 plots the RF energy provided to an acceleration unit 130 over the same period of time. At the start of the first operating cycle 190, the RF energy from the first RF energy source 132 rises from zero to a reference acceleration peak 255 value at t1 and back to zero at t3, the RF energy pulse 255 being of approximately uniform amplitude. During the rest of this first operating cycle 190, including instants t4 and t5, the RF energy is zero, or approximately zero. The waveform repeats during the second operating cycle 190.

The duration of the RF energy pulse 255 from t1 to t3 and the reference acceleration peak 255 value are predetermined and/or controlled to provide the desired acceleration of the proton beam by the RF energy during the proton beam on-time. Acceleration occurs between t1 and t3. This RF control configuration is the reference for the other three 602, 603, 604 so the reference acceleration peak 255 value is considered here to be nominally 100%. During operation according to 601, the RF energy is provided to the cavity in a single pulse per proton beam operating cycle 190 at substantially the same time as the on-time 145 of the proton beam. No substantial RF energy is provided during the proton beam off-time, so no RF compensation pulses are provided.

Compared to the waveform depicted in 501 of FIG. 5, the full pulse width from the first RF energy source 132 is used for acceleration, whereas in 501 only half the available pulse width was used. This increases efficiency because the full pulse of the first RF energy source 132 may be used for beam acceleration, allowing a longer pulse of the proton beam 115 per operating cycle 190. This advantageously may provide an increase in the dose delivered to the patient, which may reduce treatment time. Alternatively, the beam pulse length may be kept short, and the requirements in terms of pulse length for the first RF energy source 132 may be relaxed.

The second RF control configuration graph 602 plots the RF energy provided to an acceleration unit 130 over the same period of time. At the start of the first operating cycle 190, the RF energy from the first RF energy source 132 rises from zero to an acceleration peak 255 value at t1 and back down at t3, the RF energy pulse 255 being of approximately uniform amplitude. This acceleration peak 255 value is approximately 90% of the reference acceleration peak value 601. The RF energy from the first RF energy source 132 drops to zero at t3.

At approximately t3, the RF energy from the second RF energy source 232 rises from zero to a compensation peak 355 value and back down at approximately t1 of the next operating cycle 190. For clarity, a gap is depicted between the acceleration peak 255 and the compensation peak 355, but in practice this gap may be very small or even zero—each pulse originated from a distinct RF energy source. The pulses may even overlap.

The waveform repeats during the second operating cycle 190. The duration of the RF energy pulse 255 from t1 to t3 and the acceleration peak 255 value 90% are predetermined and/or controlled to provide the desired acceleration of the proton beam by the RF energy from the first RF energy source 132 during the proton beam on-time. Acceleration occurs between t1 and t3 of each operating cycle 190.

In general, the duration of the RF energy pulse 355 from t3 to t1 from the second RF energy source 232, and the compensation peak value 355 are predetermined and/or controlled to compensate for the temperature change which would be expected when the accelerating unit is operated with a lower acceleration peak 55 value compared to previous operating cycles such as in 601.

So during operation, the RF energy is provided to the cavity in two pulses per proton beam operating cycle 190—the first 255 from the first RF energy source 132 at substantially the same time as the on-time of the proton beam, and the second 355 from the second RF energy source 232 at substantially the same time as the off-time of the proton beam.

For the first RF energy source 132, the whole available pulse length, for example 5 microseconds, may be advantageously used. For the second RF energy source 232, the whole time between acceleration pulses 155, for example 5 milliseconds, may be advantageously used with a significantly lower peak power compared to the control scheme depicted in 502 of FIG. 5. This may be one thousand times smaller. The RF energy controller 180 is configured to provide the first pulse 255 for acceleration, and the second pulse 355 for compensation.

The third RF control configuration graph 603 plots the RF energy provided to an acceleration unit 130 over the same period of time. At the start of the first operating cycle 190, the RF energy from the first RF energy source 132 rises from zero to an acceleration peak 255 value at t1 and back down at t3, the RF energy pulse 255 being of approximately uniform amplitude. This acceleration peak 255 value is approximately 75% of the reference acceleration peak value 601. The RF energy from the first RF energy source 132 drops to zero at t3.

At approximately t3, the RF energy from the second RF energy source 232 rises from zero to a compensation peak 355 value and back down at approximately t1 of the next operating cycle 190. Again, for clarity, a gap is depicted between the acceleration peak 255 and the compensation peak 355, but in practice this gap may be very small or even zero. Again, as the peaks originate from distinct RF sources, they may even overlap.

The waveform repeats during the second operating cycle 190. The duration of the RF energy pulse 255 from t1 to t3 and the acceleration peak 55 value 75% are predetermined and/or controlled to provide the desired acceleration of the proton beam by the RF energy from the first RF energy source 132 during the proton beam on-time. Acceleration occurs between t1 and t3 of each operating cycle 190.

In general, the duration of the RF energy pulse 355 from t3 to t1 from the second RF energy source 232, and the compensation peak value 355 are predetermined and/or controlled to compensate for the temperature change which would be expected when the accelerating unit is operated with a lower acceleration peak 55 value compared to previous operating cycles such as in 601.

For the second RF energy source 232, the whole time between acceleration pulses 155, for example 5 milliseconds, may be advantageously used with a significantly lower peak power compared to the control scheme depicted in 503 of FIG. 5. The RF energy controller 180 is configured to provide the first pulse 255 from the first RF energy source 132 for acceleration, and the second pulse 355 from the second RF energy source 232 for compensation.

The fourth RF control configuration graph 604 plots the RF energy provided to an acceleration unit 130 over the same period of time. At the start of the first operating cycle 190, the RF energy from the first RF energy source 132 rises from zero to an acceleration peak 255 value at t1 and back down at t3, the RF energy pulse 255 being of approximately uniform amplitude. This acceleration peak 255 value is approximately 25% of the reference acceleration peak value 601. The RF energy from the first RF energy source 132 drops to zero at t3.

At approximately t3, the RF energy from the second RF energy source 232 rises from zero to a compensation peak 355 value and back down at approximately t1 of the next operating cycle 190. Again, for clarity, a gap is depicted between the acceleration peak 255 and the compensation peak 355, but in practice this gap may be very small or even zero. Again, as the peaks originate from distinct RF sources, they may even overlap.

The waveform repeats during the second operating cycle 190. The duration of the RF energy pulse 255 from t1 to t3 and the acceleration peak 55 value 25% are predetermined and/or controlled to provide the desired acceleration of the proton beam by the RF energy from the first RF energy source 132 during the proton beam on-time. Acceleration occurs between t1 and t3 of each operating cycle 190.

In general, the duration of the RF energy pulse 355 from t3 to t1 from the second RF energy source 232, and the compensation peak value 355 are predetermined and/or controlled to compensate for the temperature change which would be expected when the accelerating unit is operated with a lower acceleration peak 55 value compared to previous operating cycles such as in 601.

For the second RF energy source 232, the whole time between acceleration pulses 155, for example 5 milliseconds, may be advantageously used with a significantly lower peak power compared to a similar configuration using a single RF power source (not depicted in FIG. 5). The RF energy controller 180 is configured to provide the first pulse 255 from the first RF energy source 132 for acceleration, and the second pulse 355 from the second RF energy source 232 for compensation.

So substantially constant average power may be achieved by interspersing the compensating pulses 355, during the proton beam off-time, between the accelerating pulses 255, during the proton beam on-time 145. The time between RF energy pulses are preferably short compared to the thermal time response of the cavity. The amplitude of the accelerating pulse 255 may be varied over the full range from maximum power to nearly zero power. Likewise, the power in the compensation pulse 355 may be varied from maximum power to nearly zero power to keep the average power substantially constant.

Preferably, the expected temperature change is fully compensated, but if this is not possible due to operating constraints, partially compensating for the temperature change is still advantageous compared to the situation known in the prior art.

In general, using a second RF energy source 232 provides more flexibility because it may be controlled and operated independently of the first RF energy source 132.

The skilled person will realize that the waveforms depicted are schematic, and the actual waveforms may have a non-negligible rise and fall-time which may need to be taken into account when determining the control parameters used. Similarly, slight beam current variations may also need to be taken into account.

The skilled person will also realize that any RF energy waveform shape is possible, not just the square-wave pulses depicted. For example, a triangular or ramp-shape or any combination thereof.

The energy controller 180 may be configured to provide substantially the same or substantially different RF pulses to each accelerator unit during a particular proton beam operation cycle 190. The accelerator units may be operated individually or in groups. The RF pulses to an individual accelerator unit may also vary during the operation of the system 100 over more than one proton beam operation cycle 190. This provides a very flexible and accurate system to control and stabilize beam energy variation caused by the accelerator system 100 itself, or external disruptive elements.

The peak RF power produced by the RF energy source, such as a klystron, is consumed by two mechanisms, the power dissipated in the cavity and the power transferred to the beam. When the beam is not present in the cavity, that portion of power needs to be dissipated in the cavity. Although in medical applications the peak beam current is low, typically 300 µA (microAmpere), it may be advantageous to account for this by overcooling the cavity.

If the power dissipated in the cavity at full energy is P_cav_max and the power dissipated at reduced power is P_cav1, the energy U0 deposited in the cavity at full energy is:

$$U0 = P\_cav\_max \times \text{the pulse width } t \text{ (for square pulses), and or}$$

$$U0 = \int P(t)\text{cav\_max } dt \text{ (for pulses in general)},$$

with the appropriate corrections for the power lost during the cavity fill and decay times. The energy deposit during the reduced amplitude pulse is U1.

To prevent significant changes in cavity temperature, an additional amount of energy must be supplied within a time short compared to the thermal response time of the cavity.

This may be done on a pulse-by-pulse basis, or the additional energy may be supplied on a longer time scale, subject to the constraint that the cavity frequency fluctuations are small enough not to affect the performance of the accelerator significantly.

If the cavity energy supplied during an active beam pulse is:

$U1 = P\_cav1 * t$ (for square pulses)

and/or $U1 = \int P(t)cav1\, dt$ (for pulses in general), the additional energy that must be supplied is:

$U2 = (P\_cav\_max - P\_cav1) * t$ (for square pulses)

and/or $U2 = \int (P(t)cav\_max - P(t)cav1) dt$ (for pulses in general).

This energy U2 may be provided with any peak power and pulse length wherein, preferably, the total energy is U2, such that, averaged over times short compared to the thermal response time of the cavity, the total power dissipation, and thus the cavity temperature is substantially constant—in other words, constant within an acceptable tolerance, preferably a few tens of degree.

For full energy compensation, the second RF energy source 232 should preferably deliver at least the same average power as the first RF energy source 132. Knowing the maximum power that the first RF energy source 132 may deliver, the power of the second RF energy source 232 may be determined and/or controlled pulse-to-pulse to compensate the difference in the power of the pulses delivered by the first RF energy source 132 with respect to this maximum. In this way, the average energy every two pulses (one from the first RF energy source 132 and one from the second RF energy source 232) is kept substantially constant, and the temperature variation due to differences on energy is suppressed. The mathematical criteria in this embodiment is to keep substantially constant the integral over time (energy) by determining and/or controlling the second RF energy source 232 to follow any changes in operation of the first RF energy source 132.

It may also be advantageous to provide substantially the same RF energy 132 for each successive proton beam operating cycle 190. This provides a substantially constant average RF power to the cavity 131 during operation, increasing the proton beam energy stability over more than one operating cycle 190. The RF energy from both the first 132 and second 232 RF energy sources contribute to this constant average RF power, although operating cycles 190 may be also used in which only RF energy from the first RF energy source 132 is provided or RF energy from the second RF energy source 232 only.

FIGS. 2 and 3 depict schematically the use of a set of RF energy sources for each accelerator unit 130. However, this should not be interpreted as requiring two physical units for each accelerator unit 130—the diagrams indicate a functional requirement only. The skilled person will realize that the appropriate use of RF combiners and couplers allow RF energy to be provided to any number of accelerator units 130 using one or more energy sources. Similarly, each accelerator unit 130 may comprise one or more cavities 131.

Figure 4:
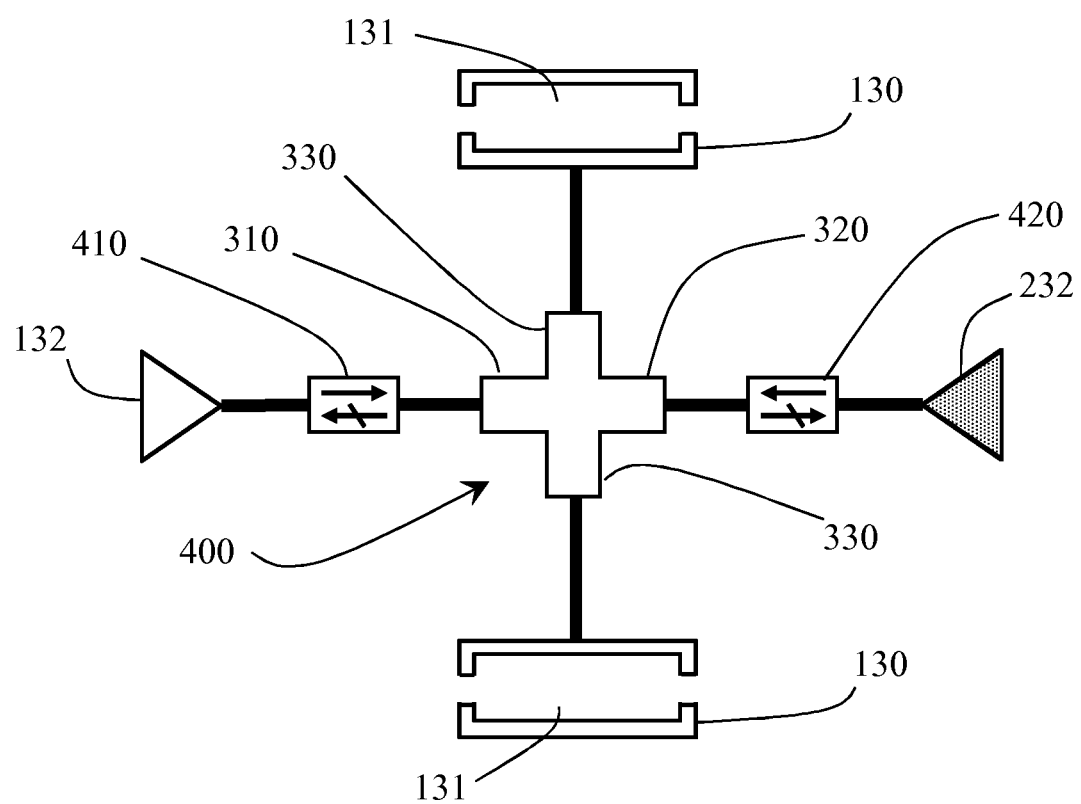
FIG. 4 depicts a second example of an accelerator unit with a cavity to which RF energy may be provided by a first and second RF source.

FIG. 4 depicts a modified FIG. 3, in which RF energy is provided to two accelerator units 130 from a first 132 and/or second 232 RF energy source during operation.

A further example of an RF coupler or combiner 400 is depicted—it is configured and arranged to transfer RF energy from the first 132 and/or second 232 RF energy source to at least two accelerator units 130 having at least one cavity 131. The RF coupler or combiner 400 comprises a first RF input 310 for receiving RF energy from the first RF source 132, a second RF input 320 for receiving RF energy from the second RF source 232; and two RF outputs 330 for providing RF energy to at least one cavity 131 each.

A suitable coupler 400 would be a so-called Magic T or hybrid tee, with the H-plane arm being configured and arranged as the second RF input 320, and the E-plane arm being configured and arranged as the first RF input 310. The advantage of a Magic T is that it may be configured and arranged such that the power entering from either the first RF input 310 or the second RF input 320 is divided substantially equally between the two RF outputs 330. In addition, Magic T may be configured and arranged such that the two RF outputs 330 are substantially isolated from each other.

Alternatively, any other suitable coupler or combiner 400 may be used, such as a rat-race coupler.

Optionally, the accelerator unit of FIG. 4 may comprise a first 410 and second 420 RF isolator to protect the RF energy source from any reflected RF power:

the first isolator 410 is configured and arranged to transfer RF energy from the first RF source 132 to the first RF input 310 of the RF coupler 300, 400, and further configured and arranged to attenuate RF energy transfer from said first RF input 310 to said first RF source 132; and the second isolator 420 is configured and arranged to transfer RF energy from the second RF source 232 to the second RF input 320 of the RF coupler 300, 400, and further configured and arranged to attenuate RF energy transfer from said second RF input 320 to said first RF source 232.

Although depicted here in combination with a coupler having two RF energy outputs 330, such isolators 410, 420 may be used downstream of a first 132 or second 232 RF energy source where required. The isolator 410, 420 may also be comprised within the RF energy source. In practice, an isolator may not fully attenuate the reflected energy—in practice approximately 1/1000 (30 dB) may still be transmitted.

Although this disclosure refers to a first RF energy source 132 and a second RF energy source 232, the skilled person will realize that more than one RF unit may be provided to provide the functionality of the first RF energy source 132 and/or a second RF energy source 232. It falls within the scope of the invention to have a plurality of physical RF units being functionally operated as a single RF source—in other words, they are all directed to produce RF pulses at substantially the same time.

The number of energy sources required depends on the number of cavities to which the energy is being provided and practical limitations of the selected RF energy source. The RF energy controller 180 may be configured and arranged to operate a plurality of RF energy sources as the first RF energy source 132, and/or a plurality of RF energy sources as the second RF energy source 232.

The accelerator units may be any suitable RF linear accelerator (or Linac), such as a Coupled Cavity Linac (CCL), a Drift Tube Linac (DTL), a Separated Drift-Tube Linac (SDTL), a Side-Coupled Linac (SCL), or a Side-Coupled Drift Tube Linac (SCDTL). They may all be the same type, or different types may be combined in cascade.

Figure 7:
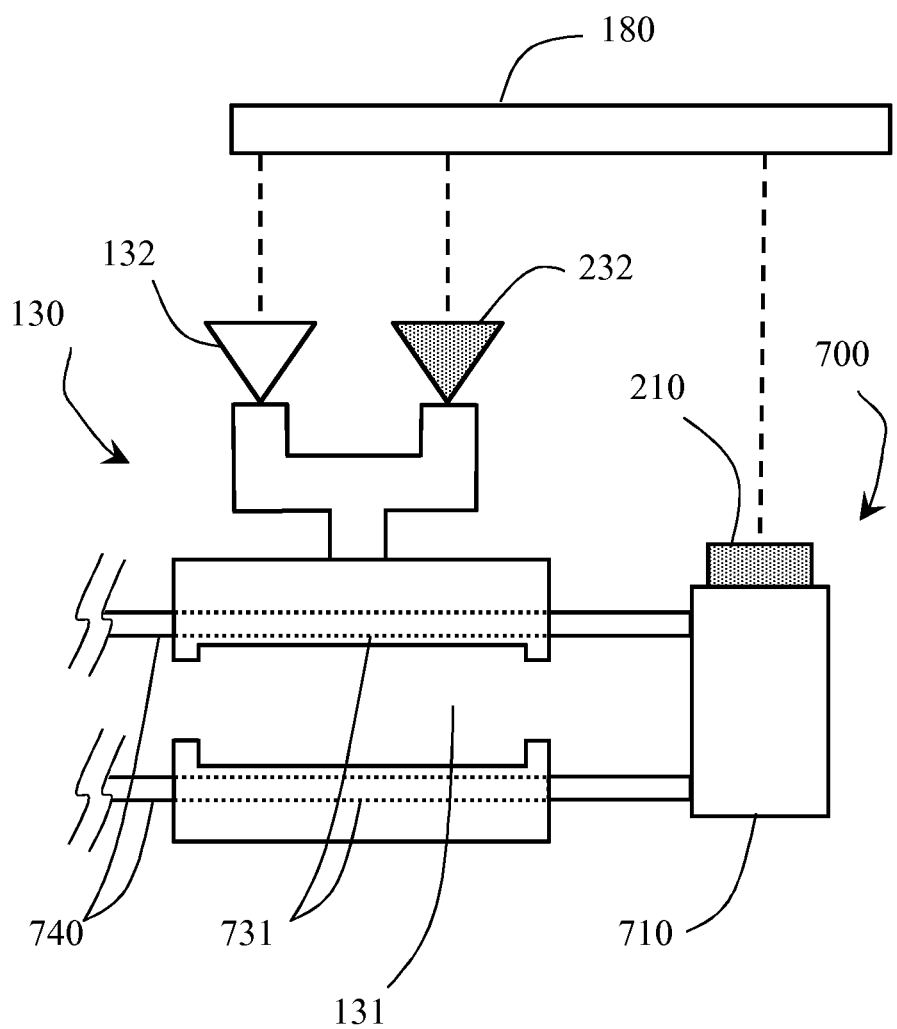
FIG. 7 shows another example of an accelerator unit according to the invention.

As mentioned above, a liquid-based temperature control system 700 may be used in combination with a second RF source 232—an example of this is depicted in FIG. 7. It comprises the accelerator unit 130, described above in relation to FIGS. 1 to 6, with the first 132 and second 232 energy source.

However, the example also includes a temperature control system 700 comprising:
- a heater 710, configured and arranged to hold a liquid, and to bring it into thermal contact with an energy source 210;
- one or more cavity wall channels 731, in fluidic communication with heater 710, disposed proximate the walls of at least one cavity 131 such that the temperature of at least a portion of the walls of at least one cavity 131 may be maintained or increased; and
- one or more liquid outlets 740, in fluidic communication with the one or more cavity wall channels 731.

The temperature control system 700 is further configured and arranged to create a flow of the liquid from the heater 710 to the one or more cavity wall channels 731 using, for example, one or more liquid pumps (not depicted).

Typically, accelerator units are provided with a cooling circuit to cool their cavities during normal operation—without this cooling, the cavities may overheat and reach very high temperatures. Water or water-based is the most common coolant liquid or fluid, and one or more cooling channels are provided close to the cavity walls and/or close to the highest temperature points.

The temperature control system 700 according to the invention may therefore comprise one or more components of a conventional cooling system, it may be comprised in a conventional cooling system or it may form a separate system to be operated in parallel with a conventional cooling system. These separate systems may share one or more cooling channels in a cavity and/or proximate a cavity wall.

Advantageously, the temperature control system 700 according to the invention may comprise (may use) the one or more cavity cooling channels typically found in cavities.

The temperature control system 700 is configured and arranged to increase or maintain the temperature of the at least one cavity 131 during the off-time of the proton beam operating cycle 190. The energy source 210 may be any suitable type which can at least be partially synchronized with the proton beam off-time, such as an electrical heat source and/or an RF energy source. As depicted, the energy source is connected to the RF energy controller 180. Additionally or alternatively, it may be connected to the beam output controller 120.

One of the insights upon which an aspect of the invention is based is that cooling of cavities may cause stability problems, and that an improvement is provided if the at least one cavity 131 is heated during the proton beam off-time.

As this is a more indirect way to heat the at least one cavity, it may be advantageous to apply some heat during the proton beam on-time, anticipating the proton beam off-time. This is a partial synchronization.

Using this indirect way of heating may be advantageous during longer periods of inactivity and/or longer periods of proton beam off-time—for example, exceeding several beam duty cycles).

In a steady state of heat transfer between the temperature control system 700 and the at least one cavity 131, the heat flux is substantially determined by the design of the temperature control system 700 and the temperature difference between the liquid and the at least one cavity 131.

$$Q = cte(TCav - TLiq)$$

where Q is the heat flux, TCav is the cavity temperature, TLiq is the liquid temperature and cte is a constant that depends on the heat transfer coefficient and the contact surface with the liquid.

By changing the liquid temperature by use of an energy source 210, the temperature of at least a portion of the walls of at least one cavity 131 is changed to keep the heat flux substantially constant.

The energy source 210 may be an electrical heat source used in an immersion heater 710. It may also be an RF energy source—this is explained in more detail in relation to FIG. 9 below.

Figure 8:
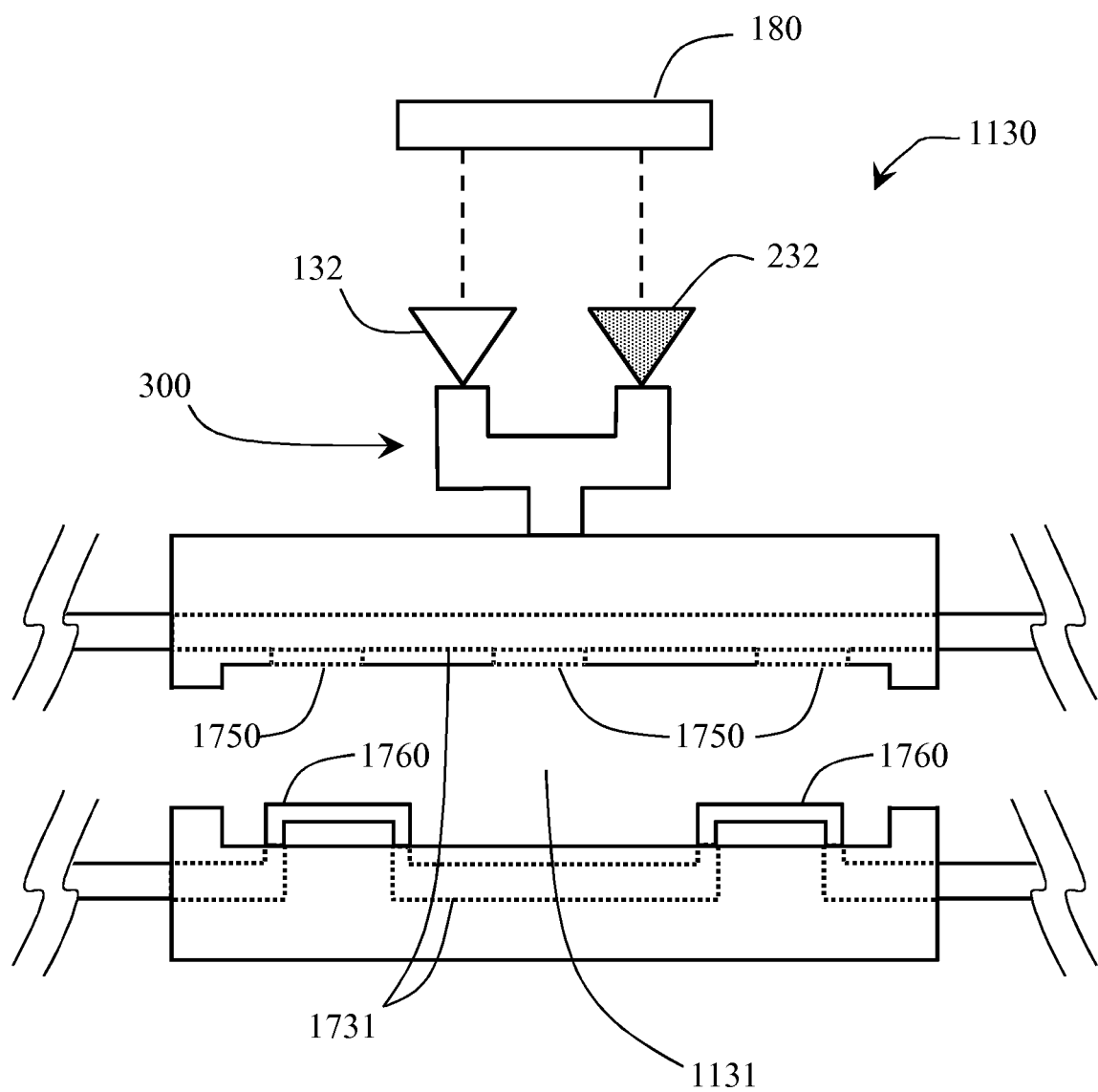
FIG. 8 shows a further example of an accelerator unit according to the invention.

FIG. 8 depicts a further example according to the invention. It comprises a modified accelerator unit 1130, which is similar to the accelerator unit 130 described above in relation to FIG. 1 to 6. It also comprises a first 132 and second 232 energy source. However, it differs as follows:
- the modified accelerator unit 1130 comprises a modified cavity 1131;
- one or more modified cavity wall channels 1731, in fluidic communication with a conventional cooling system (not depicted) for use with a liquid, disposed proximate the walls of at least one modified cavity 1131 such that the temperature of at least a portion of the walls of at least one modified cavity 1131 may be cooled;
- the one or more modified cavity wall channels 1731 are in fluidic communication with one or more cavity channel windows 1750 and/or one or more cavity channel protrusions 1760.

Additionally or alternatively, the modified cavity wall channels 1731 may be in fluidic communication with a temperature control system 700 as described above in relation to FIG. 7.

The one or more cavity channel windows 1750 and/or one or more cavity channel protrusions 1760 are configured to be one or more portions of the cavity wall channels 1731—they are configured and arranged to allow RF energy from the at least one modified cavity 1131 to increase or maintain the temperature of the liquid.

Energy transfer between the modified cavity 1131 and the liquid in channels may be provided by one or more channel portions with wall, configured to substantially absorb and/or substantially transmit at least a portion of RF energy from the at least one cavity to the liquid. These properties may be provided using one or more suitable materials and/or coatings. For example:
- a suitable carbon or ferrite may be used may be used to absorb RF and locally heat the wall
- suitable plastic or glass, such as PTFE or borosilicate glass, may be used to transmit RF. Ceramics, in particular alumina ceramics, are also available that allow RF to penetrate, but allow sealing of a chamber with liquid. It may also be advantageous to use a liquid or fluid with a relatively high RF absorption, such as water or water-based.

The one or more cavity channel protrusions 1760 are depicted as protrusions—however, similar structures may also be recessed into a wall of the modified cavity 1131.

The skilled person will realize that the presence of such windows 1750 and/or protrusions 1760 may change cavity metrics and properties—these changes may be taken into account in the design of the modified acceleration unit 1130. Any loss of efficiency may be compensated by using higher RF energies. Alternatively or additionally, the dimensions and/or disposition of the windows 1760 and/or protrusions 1760 may be selected to reduce such effects.

Alternatively or additionally, the RF coupler 300 may be modified to comprise one or more windows 1750 and/or protrusions 1760. These may be configured to absorb a predetermined portion of energy, or comprised in one or more cooling channels. A modified waterload may also be used.

The cooling system or temperature control system 700 is configured and arranged to allow RF energy from the at least one cavity 1131 to increase or maintain the temperature of the liquid during the off-time of the proton beam operating cycle 190.

For example:
one or windows 1750 and/or protrusions 1760 may be disposed in a region that is only exposed to RF energy from the second RF energy source 232, such as in one or more branches of a coupler or combiner 300, or close to the point where the RF energy enters the at least one cavity.

the cooling system or temperature control system 700 may be configured and arranged to prevent or restrict the flow of liquid through the modified cavity wall channels 1731 during the on-time of the proton bema, and allow it to flow (or restrict it less) during the off-time. For example, by using an appropriate set of valves.

Figure 9:
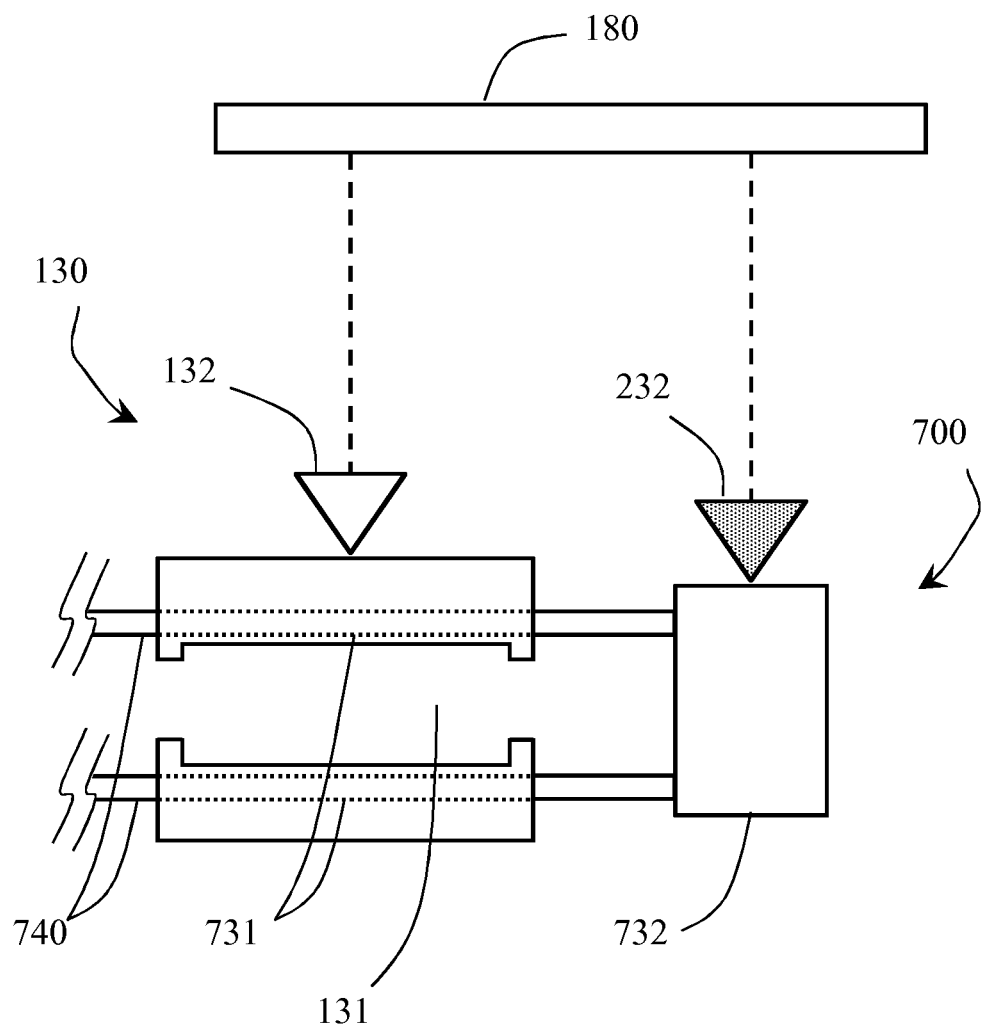
FIG. 9 shows yet another example of an accelerator unit according to the invention.

FIG. 9 depicts a further example according to the invention—a liquid-based temperature control system 700, similar to the one described above in relation to FIG. 7, may be used independently:

there is no second RF energy source, distinct from the first source 132, for providing RF energy to the at least one cavity 131 during operation; and the at least one cavity 131 is not configured for receiving RF energy from a second (232) energy source.

FIG. 9 depicts:

A proton linear accelerator system for irradiating tissue, the accelerator system comprising:

a proton source (not depicted) for providing a pulsed proton beam (not depicted) during operation;

a beam output controller (not depicted) for adjusting the beam current of the proton beam exiting the source;

an accelerator unit 130 having:
a proton beam input (not depicted) for receiving the proton beam;
a proton beam output (not depicted) for exiting the proton beam;
a first 132 RF energy source for providing RF energy during operation;
and second 232 RF energy source, distinct from the first source 132, for providing RF energy during operation;
at least one cavity 131 extending from the proton beam input to the proton beam output, for receiving RF energy from the first 132 energy source, and for coupling the RF energy to the proton beam as it passes from the beam input to the beam output;

the system further comprising:
a temperature control system 700, comprising the second RF source 232 as an energy source for adapting the temperature of the at least one cavity 131 using a liquid;

an RF energy controller 180 connected to the first 132 and second 232 RF energy source for adjusting the RF energy provided to the accelerator system;

the beam output controller 120 being configured to provide proton beam pulses with a predetermined and/or controlled beam operating cycle (not depicted);

the RF energy controller 180 being configured to provide RF energy from the first RF energy source 132 during the on-time of the proton beam operating cycle for changing the energy of the proton beam, and to provide RF energy from the second RF energy source 232 during the off-time of the proton beam operating cycle for increasing or maintaining the temperature of the at least one cavity 131.

Although the energy source depicted 232, 732 is the second RF energy source 232 comprised in an RF-powered heater, the energy source and heater may be any suitable type which can at least be partially synchronized with the proton beam off-time, such as the energy source 210 and heater 710 described above in relation to FIG. 7.

As depicted in FIG. 9, the second RF energy source 232 is connected to the RF energy controller 180. Additionally or alternatively, it may be connected to the beam output controller 120.

The use of a RF-powered heater 732, instead of a conventional electrical immersed heater, has the advantage that RF heating may be substantially faster—electrically-powered heater transfer energy to the liquid through their contact surface. With RF-powered heaters, energy is absorbed volumetrically by the liquid.

This may provide a more direct absorption of heat into the liquid, without having to first heat, for example, the walls of the heater 731, 732.

This embodiment may be less efficient in certain configurations compared to the embodiments with the second RF energy source 232 being used to provide RF energy to the at least one cavity 131 (as depicted in FIG. 3, for example). However, it is more efficient than using an electric-heater 731. This embodiment may allow a wider combination of RF sources and liquids to be used.

Alternatively or additionally, one or more of the heaters described above may be configured and arranged proximate the liquid inlet of the at least one cavity. The one or more heater may then heat the liquid and provide energy to the at least one cavity very quickly. This is even more advantageous with an RF-heater and RF energy source, which already offers a faster heating compared to conventional means.

Alternatively or additionally, one or more of the RF-heaters described above may be configured and arranged to heat the liquid and provide energy to the at least one cavity at instances that are independent of the proton beam duty-cycle—in other words, during one or more periods when the beam is off and/or during one or more periods when the beam is on. The rf-heater may then be operated relatively independently, and connections to a beam output controller 120 or an RF energy controller 180 are no longer required. This provides a faster heating compared to conventional means. The RF energy source used may also be relatively inexpensive.

It will be appreciated that the invention—especially many of the method steps indicated above—also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the system claim enumerating several means, several of these means may be embodied by one and the same item of hardware. The mere fact that certain measures are recited in mutually different dependent claims does not indicate that a combination of these measures cannot be used to advantage.

REFERENCE NUMBERS

55 RF energy accelerating pulse with first RF source
100 proton linear accelerator system
102 first acceleration stage, e.g. Radio-Frequency Quadrupole (RFQ)
104 second acceleration stage, e.g. Side-Coupled Drift Tube Linac (SCDTL)
106 third acceleration stage, e.g. Coupled Cavity Linac (CCL)
110 proton source
115 proton beam
120 beam output controller
130 accelerator unit
131 cavity
132 first RF energy source
135 proton beam input
137 proton beam output
140 axis: beam current (FIG. 4)
145 proton beam operating cycle
150 axis: period of time (FIG. 4)
155 RF energy compensation pulse with second RF source
160 Axis: RF energy (FIG. 4)
180 RF energy controller
190 proton beam operating cycle [FIGS. 5 & 6]
210 energy source
232 second RF energy source
255 RF energy accelerating pulse with first RF source
300 RF coupler or combiner
310 first RF input
320 second RF input
330 RF output
355 RF energy compensation pulse with second RF source
400 RF coupler or combiner
410 first RF isolator
420 second RF isolator
500 proton beam pulses during two operating cycles
501 first RF control configuration using first RF energy source only
502 second RF control configuration using first RF energy source only
503 third RF control configuration using first RF energy source only
504 fourth RF control configuration using first RF energy source only
601 first RF control configuration using first and second RF energy sources
602 second RF control configuration using first and second RF energy sources
603 third RF control configuration using first and second RF energy sources
604 fourth RF control configuration using first and second RF energy sources
700 temperature control system
710 heater
731 one or more cavity wall channels
732 RF-powered heater
740 liquid outlet
1130 a modified accelerator unit
1131 a modified cavity
1731 one or more modified cavity wall channels
1750 cavity channel window
1760 cavity channel protrusion

The invention claimed is:

1. A proton linear accelerator system for irradiating tissue, the accelerator system comprising:
a proton source for providing a pulsed proton beam during operation;
a beam output controller for adjusting the beam current of the proton beam exiting the source;
an accelerator unit having:
a proton beam input for receiving the proton beam;
a proton beam output for exiting the proton beam;
a first RF energy source for providing RF energy during operation;
and second RF energy source, distinct from the first source, for providing RF energy during operation;
at least one cavity extending from the proton beam input to the proton beam output, for receiving RF energy from the first and/or second energy source, and for coupling the RF energy to the proton beam as it passes from the beam input to the beam output;
the system further comprising:
an RF energy controller connected to the first and second RF energy source for adjusting the RF energy provided to the at least one cavity and further connected to the beam output controller;
the beam output controller being configured to provide proton beam pulses with a predetermined and/or controlled beam operating cycle;
the RF energy controller being configured
to provide RF energy from the first RF energy source during the on-time of the proton beam operating cycle for changing the energy of the proton beam, and
to provide RF energy from the second RF energy source during the off-time of the proton beam operating cycle for increasing or maintaining the temperature of the at least one cavity.

2. The accelerator system according to claim 1, the system further comprising an RF coupler for transferring RF energy from the first and/or second RF energy source to the at least one cavity, the RF coupler having:
a first RF input for receiving RF energy from the first RF source;
a second RF input for receiving RF energy from the second RF source; and
an RF output (330) for providing RF energy to the at least one cavity.

3. The accelerator system according to claim 2, the system further comprising:
a first isolator for transferring RF energy from the first RF source to the first RF input of the RF coupler, configured and arranged to attenuate RF energy transfer from said first RF input to said first RF source; and
a second isolator for transferring RF energy from the second RF source to the second RF input of the RF coupler, configured and arranged to attenuate RF energy transfer from said second RF input to said first RF source.

4. The accelerator system according to claim 1, wherein the RF energy controller is further configured to provide RF energy from the first RF energy source as a peak power and further configured to provide RF energy from the second RF energy source as average power.

5. The accelerator system according to claim 1, wherein the RF energy controller is further configured to provide substantially the same RF energy for each successive proton beam operating cycle.

6. The accelerator system according to claim 1, wherein the RF energy controller is further configured to provide RF energy from the first RF energy source with a first peak power and further configured to provide a successive RF energy from the second RF energy source with a second peak power, the second peak power being substantially less than the first peak power.

7. The accelerator system according to claim 1, wherein the RF energy controller is further configured to provide RF energy from the first RF energy source with a first pulse width and further configured to provide a successive RF energy from the second RF energy source with a second pulse width, the second pulse width being substantially greater than the first pulse width.

8. The accelerator system according to claim 1, wherein the RF energy controller is configured to provide a predetermined and/or controlled energy by modifying one or more of the following characteristics of the first and/or second RF energy source:
RF amplitude, RF energy on-time, RF energy off-time, RF energy pulse shape or any combination thereof.

9. The accelerator system according to claim 1, wherein the RF energy controller is further configured to provide RF energy from the first and second RF energy source at substantially the same RF frequency.

10. The accelerator system according to claim 1, the system further comprising:
a temperature control system for adapting the temperature of the at least one cavity using a liquid,
configured and arranged to increase or maintain the temperature of the at least one cavity during the off-time of the proton beam operating cycle.

11. The accelerator system according to claim 10, wherein the temperature control system comprises an energy source, configured and arranged to increase or maintain the temperature of the liquid during the off-time of the proton beam operating cycle.

12. The accelerator system according to claim 11, wherein the energy source is an electrically-heated source and/or RF-heated source.

13. The accelerator system according to claim 10, wherein the at least one cavity further comprises at least one channel portion, in fluidic communication with temperature control system, configured and arranged to allow RF energy from the at least one cavity to increase or maintain the temperature of the liquid during the off-time of the proton beam operating cycle.

14. The accelerator system according to claim 13, wherein the at least one channel portion comprises a wall, configured to substantially absorb and/or substantially transmit at least a portion of RF energy from the at least one cavity to the liquid.

15. The accelerator system according to claim 1, wherein the accelerator unit is of one of the following types:
Coupled Cavity Linac (CCL), Drift Tube Linac (DTL), Separated Drift-Tube Linac (SDTL), Side-Coupled Linac (SCL), Side-Coupled Drift Tube Linac (SCDTL).

* * * * *